United States Patent [19]

Wollweber et al.

[11] Patent Number: 5,411,987
[45] Date of Patent: May 2, 1995

[54] FUNGICIDAL SUBSTITUTED AMINO ACID AMIDES

[75] Inventors: Detlef Wollweber, Wuppertal; Thomas Seitz, Monheim; Wilhelm Brandes, Leichlingen, all of Germany

[73] Assignee: Bayer Aktiengesellschaft, Leverkusen, Germany

[21] Appl. No.: 23,241

[22] Filed: Feb. 25, 1993

Related U.S. Application Data

[62] Division of Ser. No. 514,919, Apr. 25, 1990, Pat. No. 5,210,084.

[30] Foreign Application Priority Data

May 13, 1989 [DE] Germany .................. 39 15 755.5

[51] Int. Cl.$^6$ .................. A01N 37/46; C07C 271/44
[52] U.S. Cl. .................. 514/529; 558/442; 560/115; 560/157; 560/159; 514/519; 514/530; 514/531; 514/546; 514/547; 514/548; 514/534
[58] Field of Search .................. 560/115, 157, 159; 514/534, 519, 529, 530, 531, 546, 547, 548, 534; 558/442

[56] References Cited

U.S. PATENT DOCUMENTS

| | | | |
|---|---|---|---|
| 3,393,224 | 7/1968 | Brookes et al. | 560/24 |
| 3,808,191 | 4/1974 | Poduska et al. | 514/534 |
| 4,021,224 | 5/1977 | Pallos et al. | 560/159 |
| 4,138,422 | 2/1979 | Chan et al. | 560/24 |
| 4,259,234 | 3/1981 | Smithwick, Jr. et al. | 930/20 |
| 4,322,342 | 3/1982 | Smithwick, Jr. et al. | 930/20 |
| 4,610,985 | 9/1986 | Fuhrer et al. | 560/24 |
| 4,639,468 | 1/1987 | Roncucci et al. | 560/159 |
| 4,710,514 | 12/1987 | Takahashi et al. | 514/585 |
| 4,818,748 | 4/1987 | Bendes et al. | 514/17 |
| 4,996,358 | 2/1991 | Handa et al. | 562/622 |

FOREIGN PATENT DOCUMENTS

| | | | |
|---|---|---|---|
| 0046707 | 3/1982 | European Pat. Off. | 514/534 |
| 0493683 | 11/1991 | European Pat. Off. | 514/534 |
| 2513485 | 4/1983 | France | 514/534 |
| 2741393 | 3/1978 | Germany | 514/534 |
| 0141778 | 5/1980 | Germany | 514/534 |
| 0152275 | 11/1981 | Germany | 514/534 |
| 0271052 | 3/1988 | Germany | 514/534 |
| 0536819 | 6/1973 | Switzerland | 514/534 |

OTHER PUBLICATIONS

Pirkle et al, J. of Chrom., 479 (1989) pp. 419–423.
Breslav et al, Chemical Abstracts, vol. 110, No. 15, Abstract No. 135, 676k, p. 761, Apr. 10, 1989.
M. Breslav et al, Latv. PSR Zinat. Akad. Vestis. Kim. Ser., 1988, (5), 552–6 (Translation).
Chemical Abstracts, vol. 114, No. 25, Abstract 240.604r, p. 96, Jun. 24, 1991.
Chemical Abstracts, vol. 102, No. 13, 113961 (Apr. 1, 1985).
Thaisrivongs, et al. J. Med. Chem., Vo. 29, No. 10, 1986, pp. 2080–2087.
M. Breslav et al., Latv. PSR Zinat. Akad. Vestis, Kim. Ser., 1988, (5), 552–6.

Primary Examiner—C. Warren Ivy
Assistant Examiner—Zinna N. Davis
Attorney, Agent, or Firm—Sprung Horn Kramer & Woods

[57] ABSTRACT

Combating fungi with substituted amine acid derivatives of the formula

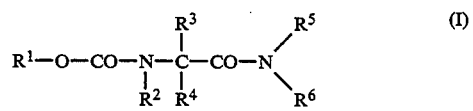

in which $R^1$ represents alkyl, alkenyl, alkinyl, halogenoalkyl, halogenoalkenyl, halogenoalkinyl, cycloalkyl or cycloalkenyl, $R^2$, $R^3$, $R^4$ and $R^5$ are identical or different and represent hydrogen, cycloalkyl or alkyl, or $R^3$ and $R^4$, together with the carbon atom to which they are bonded, form a cycloalkyl ring, and $R^6$ represents hydrogen, alkyl, alkenyl, alkinyl, cyanoalkyl, unsubstituted or substituted phenylalkyl, unsubstituted or substituted phenyl or unsubstituted or substituted cycloalkyl, or represents unsubstituted or substituted heterocyclyl or heterocyclylalkyl, or $R^5$ and $R^6$, together with the nitrogen atom to which they are bonded, represent a heterocyclyl radical, which can contain further hetero atoms.

4 Claims, No Drawings

FUNGICIDAL SUBSTITUTED AMINO ACID AMIDES

This is a division of application Ser. No. 07/514,919, filed Apr. 25, 1990, now U.S. Pat. No. 5,210,084.

The present invention relates to the use of substituted amino acid amide derivatives, some of which are known, in agents for combating pests and to new substituted amino acid amide derivatives and a process for their preparation.

The substances according to the invention and the substances to be used according to the invention have an excellent action in combating pests. The substances according to the invention and the substances to be used according to the invention can be employed in particular as fungicides, above all in plant protection.

Certain amino acid amides are already known, such as, for example, N-tert.-butoxycarbonyl-L-leucylbenzylamide (EP-A-236,874).

A use of these compounds in agents for combating pests, however, is not described.

The present application thus relates to the use of substituted amino acid amide derivatives of the general formula (I)

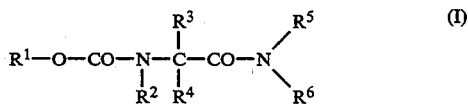

in which $R^1$ represents alkyl, alkenyl, alkinyl, halogenoalkyl, halogenoalkenyl, halogenoalkinyl, cycloalkyl or cycloalkenyl, $R^2$, $R^3$, $R^4$ and $R^5$ are identical or different and represent hydrogen, cycloalkyl or alkyl, or $R^3$ and $R^4$, together with the carbon atom to which they are bonded, form a cycloalkyl ring, and $R^6$ represents hydrogen, alkyl, alkenyl, alkinyl, cyanoalkyl, unsubstituted or substituted phenylalkyl, unsubstituted or substituted phenyl or unsubstituted or substituted cycloalkyl, or represents unsubstituted or substituted heterocyclyl or heterocyclylalkyl, or $R^5$ and $R^6$, together with the nitrogen atom to which they are bonded, represent a heterocyclyl radical, which can contain further hetero atoms, for combating pests.

The compounds of the formula (I) and of the following compounds (Ia) can furthermore contain one or more chirality centers and can thus be in the form of various enantiomer and diastereomer mixtures, which can be resolved, if appropriate, in the customary manner. Both the use of the pure enantiomers and diastereomers and that of the mixtures are likewise features of the present invention.

For simplicity, the use of compounds of the formula (I) or (Ia) is always referred to below, although both the pure compounds and the mixtures with various contents of isomeric, enantiomeric and diastereomeric compounds are meant.

Formula (I) provides a general definition of the substituted amino acid amide derivatives to be used according to the invention.

Preferably, in the general formulae below, unless defined otherwise, the radicals have the following meanings:

Alkyl, individually or in composite radicals straight-chain or branched alkyl having 1 to 6, in particular to 1 to 4, carbon atoms. Methyl, ethyl, n- and i-propyl and n-, i-, s- and t-butyl may be mentioned as examples and as preferred.

Alkenyl straight-chain or branched alkenyl having 2 to 6, in particular 2 to 4, carbon atoms. Optionally substituted ethenyl, prop-1-enyl, prop-2-enyl and but-3-enyl may be mentioned as examples and as preferred.

Alkinyl straight-chain or branched alkinyl having 2 to 6, in particular 2 to 4, carbon atoms. Optionally substituted ethinyl, prop-1-inyl, prop-2-inyl and but-3-inyl may be mentioned as examples and as preferred.

Cycloalkyl substituted or unsubstituted cycloalkyl having 3 to 7, in particular 3 to 6, carbon atoms. Cyclopropyl, cyclopentyl and cyclohexyl may be mentioned as examples and as preferred.

Cycloalkenyl substituted or unsubstituted cycloalkenyl having 3 to 7, in particular 3 to 6, carbon atoms and 1 or 2 double bonds.

Heterocyclyl substituted or unsubstituted heteroparaffinic, heteroolefinic and heteroaromatic rings having 2 to 6, in particular 4 or 5, carbon atoms and one or two, if appropriate other hetero atoms, such as nitrogen and oxygen.

Halogenoalkyl straight-chain or branched halogenoalkyl having 1 to 6, in particular 1 to 4, carbon atoms and 1 to 9, in particular 1 to 5 and above all 1 to 3, identical or different halogen atoms, such as fluorine, chlorine, bromine and iodine, in particular fluorine and chlorine. Fluoromethyl, fluoroethyl, fluoropropyl, chloropropyl, fluorobutyl, chlorobutyl, difluoromethyl, difluoroethyl, dichloroethyl, difluoropropyl, dichloropropyl, difluorobutyl, dichlorobutyl, trifluoromethyl, trichloromethyl, trifluoroethyl, trichloroethyl, trifluoropropyl, trichloropropyl, trifluorobutyl and trichlorobutyl may be mentioned as examples and as preferred.

Halogenoalkenyl and halogenoalkinyl straight-chain or branched optionally substituted halogenoalkenyl or halogenoalkinyl having 2 to 6, in particular 2 to 4, carbon atoms and 1 to 9, in particular 1 to 5 and above all 1 to 3, identical or different halogen atoms, such as fluorine, chlorine, bromine and iodine, in particular fluorine and chlorine. Fluoroallyl, chloroallyl, fluorobutenyl, chlorobutenyl, fluoropropargyl, chloropropargyl, fluorobutinyl and chlorobutinyl may be mentioned as examples and as preferred.

The optionally substituted radicals of the general formulae can carry one or more, preferably 1 to 3 and in particular 1 or 2, identical or different substituents. Substituents which may be mentioned as examples and as preferred are;

alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propoxy and n-, i-, sec.- and t-butoxy; alkylthio having preferably 1 to 4, in particular 1 or 2, carbon atoms, such as methylthio, ethylthio, n- and i-propylthio and n-, i-, sec.- and t-butylthio; halogenoalkyl, halogenoalkoxy and halogenoalkylthio having preferably 1 to 4, in particular 1 or 2, carbon atoms and preferably 1 to 9, in particular 1 to 5, halogen atoms, the halogen atoms being identical or different and halogen atoms being, preferably, fluorine, chlorine or bromine, in particular fluorine, such as trifluoromethyl, trifluoromethoxy and trifluoromethylthio; hydroxyl; halogen, preferably fluorine, chlorine, bromine and iodine, in particular fluorine, chlorine and bromine; cyano; nitro; amino; alkylamino and dialkylamino having preferably 1 to 4, in particular 1 or 2, carbon atoms per alkyl group, such as methylamino, ethylamino, dimethylamino and diethylamino; and carboxyl.

The compounds of the formula (I) which are preferably used are those in which $R^1$ represents straight-chain or branched alkyl having 1 to 6 carbon atoms, straight-chain or branched alkenyl or alkinyl having 2 to 6 carbon atoms, straight-chain or branched halogenoalkyl having 1 to 6 carbon atoms and 1 to 9 identical or different halogen atoms, straight-chain or branched halogenoalkenyl or halogenoalkinyl having 2 to 6 carbon atoms and 1 to 9 identical or different halogen atoms or substituted or unsubstituted cycloalkyl or cycloalkenyl having 3 to 7 carbon atoms, $R^2$, $R^3$, $R^4$ and $R^5$ are identical or different and represent hydrogen, unsubstituted or substituted cycloalkyl having 3 to 7 carbon atoms or straight-chain or branched alkyl having 1 to 6 carbon atoms, or $R^3$ and $R^4$, together with the carbon atom to which they are bonded, form a cycloalkyl ring having 3 to 7 carbon atoms, and $R^6$ represents hydrogen or straight-chain or branched alkyl having 1 to 6 carbon atoms, or represents alkenyl or alkinyl having in each case 2 to 6 carbon atoms, or represents cyanoalkyl having 1 to 4 carbon atoms in the alkyl part, phenylalkyl having 1 to 4 carbon atoms in the alkyl part which is unsubstituted or substituted in the phenyl part by 1 to 3 identical or different substituents, or phenyl which is unsubstituted or substituted by 1 to 3 identical or different substituents, possible substituents in each case being: halogen; alkyl, alkoxy and alkylthio having in each case 1 to 4 carbon atoms; halogenoalkyl, halogenoalkoxy and halogenoalkylthio having in each case 1 to 4 carbon atoms and 1 to 9 identical or different halogen atoms; hydroxyl; cyano, nitro, amino, alkylamino and dialkylamino having in each case 1 to 4 carbon atoms and carboxyl; or represents cycloalkyl having 3 to 7 carbon atoms which is unsubstituted or substituted by identical or different substituents, possible substituents being alkyl and alkoxy having in each case 1 to 4 carbon atoms, or represents unsubstituted or substituted heterocyclyl or heterocyclyl alkyl having 2 to 6 carbon atoms in the heterocyclyl part and one or two hetero atoms and if appropriate 1 to 4 carbon atoms in the alkyl part, possible substituents being the abovementioned phenyl substituents, or $R^5$ and $R^6$, together with the nitrogen atom to which they are bonded, represent a 5- or 6-membered heterocyclic radical, which can optionally contain oxygen or nitrogen as further hetero atoms.

Compounds of the formula (I) which are particularly preferably used are those in which $R^1$ represents straight-chain or branched alkyl having 1 to 4 carbon atoms, straight-chain or branched alkenyl or alkinyl having 2 to 4 carbon atoms, straight-chain or branched halogenoalkyl having 1 to 4 carbon atoms and 1 to 5 identical or different halogen atoms, straight-chain or branched halogenoalkenyl or halogenoalkinyl having 2 to 4 carbon atoms and 1 to 5 identical or different halogen atoms or unsubstituted or substituted cycloalkyl or cycloalkenyl having 3 to 6 carbon atoms, $R^2$, $R^3$, $R^4$ and $R^5$ are identical or different and represent hydrogen unsubstituted or substituted cycloalkyl having 3 to 6 carbon atoms or straight-chain or branched alkyl having 1 to 5 carbon atoms, or $R^3$ and $R^4$, together with the carbon atom to which they are bonded, form a cycloalkyl ring having 3 to 6 carbon atoms, and $R^6$ represents hydrogen, methyl, ethyl, allyl or propargyl, or represents cyanoalkyl having in each case 1 or 2 carbon atoms in the alkyl part; or furthermore represents phenylalkyl having 1 to 4 carbon atoms in the alkyl part which is unsubstituted in the phenyl part by one or two identical or different substituents, or represents phenyl which is unsubstituted or substituted by one or two identical or different substituents, possible substituents in each case being: fluorine, chlorine and bromine, methyl, ethyl, n- and i-propyl, n-, i-, s- and t-butyl, methoxy, ethoxy, n-and i-propoxy, n-, i-, s-and t-butoxy, methylthio, ethylthio, n- and i-propylthio, n-, i-, s- and t-butylthio, trifluoromethyl, trifluoromethoxy, trifluoromethylthio, hydroxyl, nitro, cyano, amino, methylamino, ethylamino, dimethylamino, diethylamino and carboxyl; or represents cycloalkyl having 3 to 6 carbon atoms, in each case unsubstituted or substituted by one or two identical or different substituents, possible substituents being methyl, ethyl, n- and i-propyl, n-, i-, s- and t-butyl, methoxy, ethoxy, n- and i-propoxy and n-, i-, s- and t-butoxy, or represents heterocyclyl or heterocyclylalkyl having 4 or 5 carbon atoms in the heterocyclyl part and one or two nitrogen atoms and if appropriate 1 to 4 carbon atoms in the alkyl part and being unsubstituted or substituted by one or two identical or different substituents, possible substituents being the abovementioned substituents for phenyl; or $R^5$ and $R^6$, together with the nitrogen atom to which they are bonded, represent a 5- or 6-membered heterocyclic radical, which can optionally contain oxygen or nitrogen as further hetero atoms.

Compounds of the formula (I) which are especially preferably used are those in which $R^1$ represents methyl, ethyl, n- or i-propyl, n-, i-, s- or t-butyl, fluoromethyl, fluoroethyl, fluoropropyl, chloropropyl, fluorobutyl, chlorobutyl, difluoromethyl, difluoropropyl, dichloropropyl, difluorobutyl, dichlorobutyl, trifluoromethyl, trichloromethyl, trifluoroethyl, trichloroethyl, trifluoropropyl, trichloropropyl, trifluorobutyl, trichlorobutyl, allyl, butenyl, propargyl, butinyl, fluoro- or chloro-allyl, -butenyl, -propargyl, -butinyl, cyclopropyl, cyclopentyl, cyclohexyl, cyclopentenyl or cyclohexenyl, $R^2$ represents hydrogen or methyl, $R^3$ and $R^4$ are identical or different and represent hydrogen, methyl, ethyl, n- or i-propyl, n-, i-, s- or t-butyl, 3-pentyl, cyclopropyl, cyclopentyl or cyclohexyl, or $R^3$ and $R^4$, together with the carbon atom to which they are bonded, form a cyclopropyl, cyclopentyl or cyclohexyl ring, $R^5$ represents hydrogen or methyl and $R^6$ represents hydrogen, methyl, ethyl, allyl or propargyl, or represents cyanoalkyl having in each case 1 or 2 carbon atoms in the alkyl part, or represents benzyl, 1-phenethyl, 2-phenethyl or 1-phenylpropyl, 2-phenylpropyl, 3-phenylpropyl, 1-phenylisopropyl, 2-phenylisopropyl or 1-phenyl-n-, -i- or -s-butyl which is unsubstituted or substituted in the phenyl part by one or two identical or different substituents, or represents phenyl which is unsubstituted or substituted by one or two identical or different substituents, possible substituents in each case being: fluorine, chlorine, bromine, methyl, ethyl, n- and i-propyl, n- i-, s- and t-butyl, methoxy, ethoxy, n- and i-propoxy, n-, i-, s- and t-butoxy, methylthio, ethylthio, n- and i-propylthio, n-, i-, s- and t-butylthio, trifluoromethyl, trifluoromethoxy, trifluoromethylthio, hydroxy, nitro, cyano, amino, methylamino, ethylamino, dimethylamino and diethylamino; or represents cyclopropyl, cyclopentyl or cyclohexyl, in each case unsubstituted or substituted by one or two identical or different methyl radicals; or represents pyridyl, pyridylmethyl or 1-or 2-pyridylethyl which is unsubstituted or substituted by one or two identical or different radicals, possible substituents being the abovementioned substituents for phenyl; or $R^5$ and $R^6$, together with the nitrogen atom to which they are bonded, represent a 5- or 6-membered heterocyclic radical, which can optionally contain oxygen or further nitrogen atoms.

The new substituted amino acid amide derivatives of the general formula (Ia) are used above all.

The application thus furthermore relates to new substituted amino acid amide derivatives of the general formula (Ia)

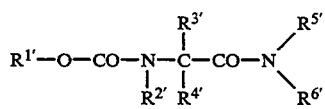
(Ia)

in which $R^{1'}$ represents alkyl, alkenyl, alkinyl, halogenoalkyl, halogenoalkenyl, halogenoalkinyl, cycloalkyl or cycloalkenyl, $R^{2'}$ and $R^{5'}$ are identical or different and represent hydrogen or alkyl, $R^{3'}$ represents hydrogen and $R^{4'}$ represents i-propyl, i-butyl, s-butyl, 3-pentyl or cycloalkyl, or $R^{3'}$ and $R^{4'}$, together with the carbon atom to which they are bonded, form a cycloalkyl ring, and $R^{6'}$ represents hydrogen, alkyl, alkenyl, alkinyl, cyanoalkyl, unsubstituted or substituted phenylalkyl, unsubstituted or substituted phenyl or unsubstituted or substituted cycloalkyl, or represents unsubstituted or substituted heterocyclyl or heterocyclylalkyl, or $R^{5'}$ and $R^{6'}$, together with the nitrogen atom to which they are bonded, represent a heterocyclyl radical which can contain further hetero atoms, excluding compounds in which a) $R^{4'}$ represents i-butyl and
$R^{1'}$ represents methyl or t-butyl and
$R^{2'}$ represents hydrogen and
$R^{5'}$ represents hydrogen or methyl and
$R^{6'}$ represents hydrogen, methyl, ethyl, phenyl, benzyl, 2-phenethyl or pyridylmethyl or
$R^{5'}$ and $R^{6'}$ form a cyclohexyl ring and b) $R^{4'}$ represents s-butyl and
$R^{1'}$ represents t-butyl and
$R^{2'}$ represents hydrogen and
$R^{5'}$ represents hydrogen and
$R^{6'}$ represents hydrogen or benzyl and c) $R^{4'}$ represents i-propyl and $R^{1'}$ represents methyl, ethyl or t-butyl and
$R^{2'}$ represents hydrogen and
$R^{5'}$ represents hydrogen and
$R^{6'}$ represents hydrogen, methyl, phenyl or benzyl or
$R^{5'}$ and $R^{6'}$ represent a cyclopentyl ring.

The compounds of the formula (Ia) can moreover contain one or more chirality centers and can thus be in the form of various enantiomer and diastereomer mixtures, which can be resolved, if appropriate, in the customary manner. Both the pure enantiomers and diastereomers and the mixtures are claimed according to the invention.

For simplicity, compounds of the formula (Ia) are always referred to below, although both the pure compounds and the mixtures having varying contents of isomeric, enantiomeric and diastereomeric compounds are intended.

Preferred compounds of the formula (Ia) are those in which $R^{1'}$ represents straight-chain or branched alkyl having 1 to 6 carbon atoms, straight-chain or branched alkenyl or alkinyl having 2 to 6 carbon atoms, straight-chain or branched halogenoalkyl having 1 to 6 carbon atoms and 1 to 9 identical or different halogen atoms, straight-chain or branched halogenoalkenyl or halogenoalkinyl having 2 to 6 carbon atoms and 1 to 9 identical or different halogen atoms or unsubstituted or substituted cycloalkyl or cycloalkenyl having 3 to 7 carbon atoms, $R^{2'}$ and $R^{5'}$ are identical or different and represent hydrogen or alkyl having 1 to 6 carbon atoms, $R^{3'}$ represents hydrogen and $R^{4'}$ represents i-propyl, i-butyl, s-butyl or 3-pentyl, or $R^{3'}$ and $R^{4'}$, together with the carbon atom to which they are bonded, form a cycloalkyl ring having 3 to 7 carbon atoms and $R^{6'}$ represents hydrogen or straight-chain or branched alkyl having 1 to 6 carbon atoms, or represents alkenyl or alkinyl having in each case 2 to 6 carbon atoms, or represents cyanoalkyl having 1 to 4 carbon atoms in the alkyl part, phenylalkyl having 1 to 4 carbon atoms in the alkyl part, which is unsubstituted or substituted in the phenyl part by one to three identical or different substituents, or phenyl which is unsubstituted or substituted by one to three identical or different substituents, possible substituents in each case being: halogen; alkyl, alkoxy and alkylthio having in each case 1 to 4 carbon atoms; halogenoalkyl, halogenoalkoxy and halogenoalkylthio having in each case 1 to 4 carbon atoms and 1 to 9 identical or different halogen atoms; hydroxyl; cyano, nitro, amino, alkylamino and dialkylamino having in each case 1 to 4 carbon atoms and carboxyl; or represents cycloalkyl having 3 to 7 carbon atoms which is unsubstituted or substituted by identical or different substituents, possible substituents being alkyl and alkoxy having in each case 1 to 4 carbon atoms, or represents unsubstituted or substituted heterocyclyl or heterocyclylalkyl having 2 to 6 carbon atoms in the heterocyclyl part and one or two hetero atoms and if appropriate 1 to 4 carbon atoms in the alkyl part, possible substituents being the abovementioned substituents for phenyl, or $R^{5'}$ and $R^{6'}$, together with the nitrogen atom to which they are bonded, represent a 5- or 6-membered heterocyclic radical, which can optionally contain oxygen or nitrogen as further hetero atoms.

Particularly preferred compounds of the formula (Ia) are those in which

R$^{1'}$ represents straight-chain or branched alkyl having 1 to 4 carbon atoms, straight-chain or branched alkenyl or alkinyl having 2 to 4 carbon atoms, straight-chain or branched halogenoalkyl having 1 to 4 carbon atoms and 1 to 5 identical or different halogen atoms, straight-chain or branched halogenoalkenyl or halogenoalkinyl having 2 to 4 carbon atoms and 1 to 5 identical or different halogen atoms or unsubstituted or substituted cycloalkyl or cycloalkenyl having 3 to 6 carbon atoms, R$^{2'}$ and R$^{5'}$ are identical or different and represent hydrogen, methyl or ethyl, R$^{3'}$ represents hydrogen and R$^{4'}$ represents i-propyl, i-butyl, s-butyl or 3-pentyl, or R$^{3'}$ and R$^{4'}$, together with the carbon atom to which they are bonded, form a cycloalkyl ring having 3 to 6 carbon atoms, and R$^{6'}$ represents hydrogen, methyl, ethyl, allyl or propargyl, or represents cyanoalkyl having 1 or 2 carbon atoms in the alkyl part; or furthermore represents phenylalkyl having 1 to 4 carbon atoms in the alkyl part, which is unsubstituted or substituted in the phenyl part by one or two identical or different substituents, or represents phenyl which is unsubstituted or substituted by one or two identical or different substituents, possible substituents in each case being: fluorine, chlorine and bromine, methyl, ethyl, n- and i-propyl, n-, i-, s- and t-butyl, methoxy, ethoxy, n- and i-propoxy, n-, i-, s-and t-butoxy, methylthio, ethylthio, n- and i-propylthio, n-, i-, s- and t-butylthio, trifluoromethyl, trifluoromethoxy, trifluoromethylthio, hydroxyl, nitro, cyano, amino, methylamino, ethylamino, dimethylamino, diethylamino and carboxyl; or represents cycloalkyl having 3 to 6 carbon atoms, in each case unsubstituted or substituted by one or two identical or different substituents, possible substituents being methyl, ethyl, n- and i-propyl, n-, i-, s- and t-butyl, methoxy, ethoxy, n- and i-propoxy and n-, i-, s- and t-butoxy, or represents heterocyclyl or heterocyclylalkyl having 4 or 5 carbon atoms in the heterocyclyl part and one or two nitrogen atoms and if appropriate 1 to 4 carbon atoms in the alkyl part and being unsubstituted or substituted by one or two identical or different substituents, possible substituents being the abovementioned substituents for phenyl; or R$^{5'}$ and R$^{6'}$, together with the nitrogen atom to which they are bonded, represent a 5- or 6-membered heterocyclic radical, which can optionally contain oxygen or nitrogen as further hereto atoms.

Especially preferred compounds of the formula (Ia) are those in which

R$^{1'}$ represents straight-chain or branched alkyl having 1 to 4 carbon atoms, straight-chain or branched alkenyl or alkinyl having 2 to 4 carbon atoms, straight-chain or branched halogenoalkyl having 1 to 4 carbon atoms and 1 to 5 identical or different halogen atoms, straight-chain or branched halogenoalkenyl or halogenoalkinyl having 2 to 4 carbon atoms and 1 to 5 identical or different halogen atoms or unsubstituted or substituted cycloalkyl or cycloalkenyl having 3 to 6 carbon atoms, R$^{2'}$, R$^{3'}$ and R$^{5'}$ represent hydrogen, R$^{4'}$ represents i-propyl, i-butyl, s-butyl or 3-pentyl, R$^{6'}$ represents phenylalkyl having 1 to 4 carbon atoms in the alkyl part, which is unsubstituted or substituted in the phenyl part by one or two identical or different substituents, possible substituents being: fluorine, chlorine and bromine, methyl, ethyl, n- and i-propyl, n-, i-, s- and t-butyl, methoxy, ethoxy, n- and i-propoxy, n-, i-, s- and t-butoxy, methylthio, ethylthio, n- and i-propylthio, n-, i-, s- and t-butylthio, trifluoromethyl, trifluoromethoxy, trifluoromethylthio, cyano, dimethylamino, diethylamino and carboxyl; or represents heterocyclyl or heterocyclylalkyl having 4 or 5 carbon atoms in the heterocyclyl part and one or two nitrogen atoms and if appropriate 1 to 4 carbon atoms in the alkyl part and being unsubstituted or substituted by one or two identical or different substituents, possible substituents being the abovementioned substituents for phenyl.

Very especially preferred compounds of the formula (Ia) are those in which

R$^{1'}$ represents methyl, ethyl, n- or i-propyl, n-, i-, s- or t-butyl, fluoromethyl, fluoroethyl, fluoropropyl, chloropropyl, fluorobutyl, chlorobutyl, difluoromethyl, difluoropropyl, dichloropropyl, difluorobutyl, dichlorobutyl, trifluoromethyl, trichloromethyl, trifluoroethyl, trichloroethyl, trifluoropropyl, trichloropropyl, trifluorobutyl, trichlorobutyl, allyl, butenyl, propargyl, butinyl, fluoro- or chloro-allyl, -butenyl, -propargyl, -butinyl, cyclopropyl, cyclopentyl, cyclohexyl, cyclopentenyl or cyclohexenyl, R$^{2'}$, R$^{3'}$ and R$^{5'}$ represent hydrogen, R$^{4'}$ represent i-propyl, i-butyl, s-butyl or 3-pentyl, R$^{6'}$ represents benzyl, 1-phenethyl, 2-phenethyl or 1-phenylpropyl, 2-phenylpropyl, 3-phenylpropyl, 1phenylisopropyl, 2-phenylisopropyl or 1-phenyl-n-, -i- or -s-butyl, which is unsubstituted or substituted in the phenyl part by one or two identical or different substituents, possible substituents in each case being: fluorine, chlorine, bromine, methyl, ethyl, n- and i-propyl, n-, i-, s- and t-butyl, methoxy, ethoxy, n- and i-propoxy, n-, i-, s- and t-butoxy, methylthio, ethylthio, n- and i-propylthio, n-, i-, s- and t-butylthio, trifluoromethyl, trifluoromethoxy, trifluoromethylthio, cyano, dimethylamino and diethylamino; or represents pyridylmethyl or 1- or 2-pyridylethyl which is unsubstituted or substituted by one or two identical or different substituents, possible substituents being the abovementioned substituents for phenyl.

The substituted amino acid amide derivatives of the general formula (Ia)

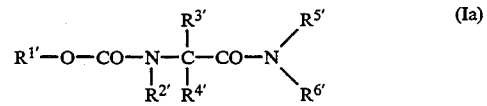

in which

R$^{1'}$ represents alkyl, alkenyl, alkinyl, halogenoalkyl, halogenoalkenyl, halogenoalkinyl, cycloalkyl or cycloalkenyl, R$^{2'}$ and R$^{5'}$ are identical or different and represent hydrogen or alkyl, R$^{3'}$ represents hydrogen and R$^{4'}$ represents i-propyl, i-butyl, s-butyl, 3-pentyl or cycloalkyl, or R$^{3'}$ and R$^{4'}$, together with the carbon atom to which they are bonded, form a cycloalkyl ring, and R$^{6'}$ represents hydrogen, alkyl, alkenyl, alkinyl, cyanoalkyl, unsubstituted or substituted phenylalkyl, unsubstituted or substituted phenyl or unsubstituted or substituted cycloalkyl, or represents unsubstituted or substituted heterocyclyl or heterocyclylalkyl, or $R^{5'}$ and $R^{6'}$, together with the nitrogen atom to which they are bonded, represent a heterocyclyl radical which can contain further hetero atoms, excluding compounds in which a) $R^{4'}$ represents i-butyl and
$R^{1'}$ represents methyl or t-butyl and
$R^{2'}$ represents hydrogen and
$R^{5'}$ represents hydrogen or methyl and
$R^{6'}$ represents hydrogen, methyl, ethyl, phenyl, benzyl, 2-phenethyl or pyridylmethyl or
$R^{5'}$ and $R^{6'}$ form a cyclohexyl ring and b) $R^{4'}$ represents s-butyl and
$R^{1'}$ represents t-butyl and
$R^{2'}$ represents hydrogen and
$R^{5'}$ represents hydrogen and
$R^{6'}$ represents hydrogen or benzyl and c) $R^{4'}$ represents i-propyl and
$R^{1'}$ represents methyl, ethyl or t-butyl and
$R^{2'}$ represents hydrogen and
$R^{5'}$ represents hydrogen and
$R^{6'}$ represents hydrogen, methyl, phenyl or benzyl or
$R^{5'}$ and $R^{6'}$ represent a cyclopentyl ring, are obtained by a process in which a substituted amino acid of the formula (II)

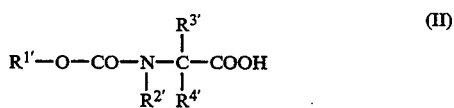

in which
$R^{1'}$, $R^{2'}$, $R^{3'}$ and $R^{4'}$ have the abovementioned meanings, or carboxy-activated derivatives thereof, is reacted with an amine of the formula (III)

in which
$R^{5'}$ and $R^{6'}$ have the abovementioned meanings, if appropriate in the presence of a catalyst, if appropriate in the presence of an acid-binding agent and if appropriate in the presence of a diluent.

The amino acid derivatives of the general formula (I) in which
$R^1$, $R^2$, $R^3$, $R^4$, $R^5$ and $R^6$ have the abovementioned meanings, can likewise be prepared by this process.

If, for example, tert.-butoxycarbonyl-D/L-valine and 4-methoxy-1-phenylethylamine are used as starting substances, the course of the process according to the invention can be represented by the following equation:

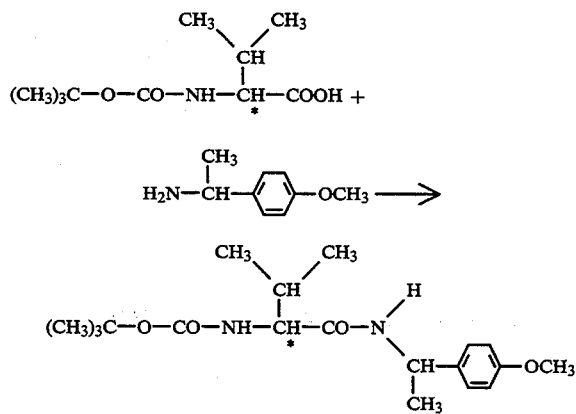

Formula (II) provides a general definition of the amino acid derivatives to be used as starting substances for carrying out the process according to the invention. In this formula, $R^{1'}$, $R^{2'}$, $R^{3'}$ and $R^{4'}$ preferably have the meanings which have already been mentioned as preferred for these substituents in connection with the description of the substances of the formula (Ia) according to the invention.

The amino acid derivatives of the formula (II) are generally known (compare, for example, Houben-Weyl, Methoden der organischen Chemie (Methods of Organic Chemistry), Volume XV, Part 1 and 2, pages 46 et seq. and 112 et seq., Georg Thieme Verlag, Stuttgart 1974; D. Keller et al., Org. Synth. 60, 2145 (1981); and R. C. Sheppard, A Specialist Periodical Report, Amino-Acids, Peptides and Proteins, The Royal Society of Chemistry, Burlington House, London 1978, and I. P. Greenstein and M. Winitz, Chemistry of Amino Acids, I. Wiley Sons Inc., New York, London 1961; and E. Schröder and K. Lübke, The Peptides Volume I, Academic Press, New York, London 1965) or can be obtained by the processes described therein.

The carboxy-activated derivatives of the amino acid of the formula (II) furthermore to be used as starting substances for carrying out the process according to the invention are generally known.

Possible carboxy-activated derivatives of the amino acids of the formula (II) are all the carboxy-activated derivatives, such as acid halides, such as, for example, acid chlorides, acid azides and furthermore symmetric and mixed anhydrides, such as, for example, the mixed O-alkylcarbonic acid anhydrides, and moreover activated esters, such as, for example, p-nitrophenyl esters or N-hydroxysuccinimide esters, as well as activated forms of the amino acids produced in situ with condensing agents, such as, for example, dicyclohexylcarbodiimide or carbonyldiimidazole.

The acid chlorides and mixed anhydrides corresponding to the amino acids of the formula (II) are preferably employed. They can be prepared by reacting the amino acids of the formula (II) or salts thereof with a halogenating agent or one of the generally known agents for the preparation of mixed anhydrides, such as, for example, phosphorus pentachloride, thionyl chloride, oxalyl chloride or isobutyl chloroformate, in a generally known manner. The use of isobutyl chloroformate is preferred.

The reaction can be carried out in the presence of inert diluents, such as, for example, aromatic, non-aromatic or halogenated hydrocarbons, such as: ketones, such as, for example, acetone; esters, such as, for example, ethyl acetate; amides, such as, for example, dimethylformamide-, nitriles, such as, for example, acetonitrile, chlorohydrocarbons, such as, for example, methylene chloride, hydrocarbons, such as, for example, toluene; or ethers, such as, for example, tetrahydrofuran or mixtures thereof, and/or in the presence of an acid-binding agent, such as, preferably, a tertiary amine, such as, for example, triethylamine, pyridine or N-methylpiperidine, at temperatures from $-78°$ C. to $100°$ C., preferably $-60°$ C. to $25°$ C.

Formula (III) provides a general definition of the amines furthermore to be used as starting substances for carrying out the process according to the invention. In these formulae, $R^{5'}$ and $R^{6'}$ have the abovementioned meanings.

The amines of the formula (III) are generally known compounds of organic chemistry.

Possible diluents for the process according to the invention are inert organic solvents, such as: ketones, such as acetone or ethyl methyl ketone; esters, such as ethyl or methyl acetate; amides, such as dimethylformamide; nitriles, such as acetonitrile; chlorohydrocarbons, such as methylene chloride or carbon tetrachloride; hydrocarbons, such as toluene; or ethers, such as tetrahydrofuran and if appropriate water and mixtures thereof.

Possible acid-binding agents for the process according to the invention are the customary inorganic and organic acid-binding agents. These include, preferably, tertiary amines, such as triethylamine, pyridine or N-methylpiperidine, and inorganic bases, for example metal hydroxides, such as sodium hydroxide and potassium hydroxide, or metal carbonates, such as sodium carbonate or calcium carbonate.

If appropriate, the process according to the invention is carried out in the presence of a catalyst. Examples which may be mentioned are 4-dimethylaminopyridine, 1-hydroxy-benzotriazole or dimethylformamide.

The temperatures can be varied within a substantial range in carrying out the process. The process is in general carried out between −78° and +120° C., preferably at −60° to +40° C.

Equimolar amounts are preferably used for carrying out the process according to the invention.

The amino acid derivatives of the formula (II) are employed here as pure optical isomers (D- or L-form) or as racemates.

The invention relates both to the pure isomers and to the mixtures. These mixtures can be resolved into the components by customary methods, for example selective crystallization on suitable solvents or chromatography on silica gel or aluminiumoxide. Racemates can be resolved into the individual enantiomers by customary methods, thus, for example, by salt formation with optically active acids, such as champhorsulphonic acid or dibenzoyltartaric acid, and selective crystallization or by derivatization with suitable optically active reagents, resolution of the diastereomeric derivatives and re-splitting or resolution of optically active column material.

The active compounds of the formulae (Ia) and (I) according to the invention and those which are known exhibit a potent action against pests and can be employed in practice for combating undesirable harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*; Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Peronospora species, such as, for example, *Peronospora pisi* or *P. brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus*;

Puccinia species, such as, for example, *Puccinia recondita*;

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Alternaria species, such as, for example, *Alternaria brassicae* and

Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be employed with particularly good success here protectively and systemically for combating Phytophthora species on tomatoes or Plasmopara species on vines and for combating rice diseases, such as, for example, against the rice spot disease causative organism (*Pyricularia oyrzae*) or against the rice stem disease causative organism (*Pellicularia sasakii*).

The active compounds are furthermore suitable for controlling animal pests, preferably arthropods, in particular insects, which are encountered in agriculture, in forestry, in the protection of stored products and of materials, and in the hygiene field. They are active against normally sensitive and resistant species and against all or some stages of development. The above-mentioned pests include:

From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusiani, Carpocapsa pomonella, Pieris spp., Chilo spp., Pyrausta nubilalis, Ephestia kuehniella, Galleria mellcnella, Tineola bissellielia, Tinea

*pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobiumpunctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.*

From the order of the Hymenoptera, for example, *Diprion spp., Hoplocampa spp., Lasius spp., Monomorium pharaonis* and *Vespa spp.*

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungitides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

For the treatment of animal pests, the active compound concentrations are in general between 0.0000001 to 95% of active compound, preferably between 0.0001 and 10%.

PREPARATION EXAMPLES

Example 1

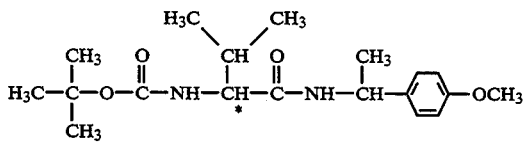

2.3 g (0.023 mol) of N-methylpiperidine are added to 5.0 g of t-butoxycarbonyl-L-valine (0.023 mol), dissolved in 50 ml of $CH_2Cl_2$, at $-20°$ C. 3.2 g (0.023 mol) of isobutyl chloroformate are then rapidly added dropwise at $-20°$ C., the mixture is subsequently stirred at the same temperature for 10 minutes and cooled to $-60°$ C. and 3.5 g (0.023 mol) of 4-methoxy-1-phenylethylamine are allowed to run in, the temperature being kept below −15° C. After 2 hours at −15° C., the mixture is subsequently stirred at room temperature for 15 hours, the solid is filtered off and rinsed with CH$_2$Cl$_2$, the filtrate is concentrated, the residue is introduced into water, the mixture is extracted twice with ethyl acetate and the combined ethyl acetate phases are washed with NaHCO$_3$ solution and water, dried and concentrated. 17.5 g (85% of theory) of N-(t-butoxycarbonyl)-L-valine 4-methoxy-1-phenylethylamide of melting point 126°–127° C. are obtained.

The following compounds of the formula (Ia) are obtained analogously to Example 1:

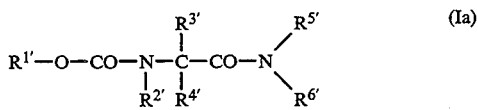

TABLE 1

| No. | R¹' | R²' | R³' | R⁴' | R⁵' | R⁶' | physical constants | amino acid employed |
|---|---|---|---|---|---|---|---|---|
| 2 | $(CH_3)_3C-$ | H | H | $-CH(CH_3)_2$ | $CH_3$ | $-CH(CH_3)-$(4-Cl-C₆H₄) | NMR: δ 0.9–1.0/ 1.4–1.5/ 7.1–7.4 | Boc-L-Valine |
| 3 | $(CH_3)_3C-$ | H | H | $-CH(CH_3)_2$ | H | $-CH(CH_3)-$C₆H₅ | melting point: 119–120° C. | Boc-L-Valine |
| 4 | $(CH_3)_3C-$ | H | H | $-CH(CH_3)_2$ | H | $-CH(CH_3)-$(4-CH₃-C₆H₄) | melting point: 139–140° C. | Boc-L-Valine |
| 5 | $(CH_3)_3C-$ | H | H | $-CH(CH_3)_2$ | H | $-CH(CH_3)-$(3,4-diCl-C₆H₃) | melting point: 95–100° C. | Boc-L-Valine |
| 6 | $(CH_3)_3C-$ | H | H | $-CH(CH_3)_2$ | H | $-CH(CH_3)-$(2-Cl-C₆H₄) | melting point: 146–147° C. | Boc-L-Valine |
| 7 | $(CH_3)_3C-$ | H | H | $-CH(CH_3)_2$ | H | $-CH(C_2H_5)-$(4-Cl-C₆H₄) | melting point: 150–151° C. | Boc-L-Valine |
| 8 | $(CH_3)_3C-$ | H | H | $-CH(CH_3)_2$ | H | $-CH(CH_3)^*-$(4-Cl-C₆H₄) | melting point: 137–138° C. *: R–(+)– | Boc-L-Valine |
| 9 | $(CH_3)_3C-$ | H | H | $-CH(CH_3)_2$ | H | $-CH_2-CH_2-$(4-Cl-C₆H₄) | melting point: 172–174° C. | Boc-L-Valine |

TABLE 1-continued

| No. | R¹ | R² | R³ | R⁴ | R⁵ \ N / R⁶ | | physical constants | amino acid employed |
|---|---|---|---|---|---|---|---|---|
| 10 | (CH₃)₃C— | H | H | —CH(CH₃)₂ | H |  —CH₂—CH₂— | melting point: 166–167° C. | Boc-L-Valine |
| 11 | (CH₃)₃C— | H | H | —CH(CH₃)₂ | CH₃ | 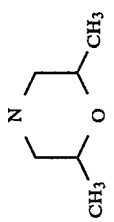 —CH₂—CH₂— | NMR: δ 0.8–1.0/ 1.4/ 3.4–3.6 | Boc-L-Valine |
| 12 | (CH₃)₃C— | H | H | —CH(CH₃)₂ | H | H | melting point: 154–156° C. | Boc-L-Valine |
| 13 | (CH₃)₃C— | H | H | —CH(CH₃)₂ | CH₃ | CH₃ | NMR: δ 0.8–1.0/ 1.4/ 2.95–3.1 | Boc-L-Valine |
| 14 | (CH₃)₃C— | H | H | —CH(CH₃)₂ | C₂H₅ | C₂H₅ | NMR: δ 0.9–1.0/ 1.1/1.2/ 1.4 | Boc-L-Valine |
| 15 | (CH₃)₃C— | H | H | —CH(CH₃)₂ | H | CH₃ | melting point: 130–131° C. | Boc-L-Valine |
| 16 | (CH₃)₃C— | H | H | —CH(CH₃)₂ | CH₃ \ N / CH₃ (morpholine with 2,6-diCH₃) | | NMR: δ 0.8–1.0/ 1.2–1.3/ 1.4 | Boc-L-Valine |
| 17 | (CH₃)₃C— | H | H | —CH(CH₃)₂ | H | C₂H₅ | melting point: 121–122° C. | Boc-L-Valine |
| 18 | (CH₃)₃C— | H | H | —CH(CH₃)₂ | pyrrolidine | | NMR: δ 0.9–1.0/ 1.4/ 1.8–2.0 | |
| 19 | (CH₃)₃C— | H | H | —CH(CH₃)₂ | H | 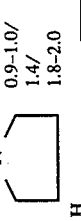 —CH₂— | melting point: 123–124° C. | Boc-L-Valine |

TABLE 1-continued

| No. | R¹' | R²' | R³' | R⁴ | $\overset{R^5}{\underset{}{\diagdown}}N\overset{R^6}{\underset{}{\diagup}}$ | | physical constants | amino acid employed |
|---|---|---|---|---|---|---|---|---|
| 20 | (CH₃)₃C— | H | H | —CH(CH₃)₂ | H | —CH₂—C₆H₄—CH₃ (p) | melting point: 143–144° C. | Boc-L-Valine |
| 21 | (CH₃)₃C— | H | H | —CH(CH₃)₂ | H | —CH₂—C₆H₄—Cl (p) | melting point: 124–125° C. | Boc-L-Valine |
| 22 | (CH₃)₃C— | H | H | —CH(CH₃)₂ | H | —CH₂—C₆H₃(Cl)₂ (3,4) | melting point: 112–113° C. | Boc-L-Valine |
| 23 | (CH₃)₃C— | H | H | —CH(CH₃)₂ | H | —CH₂—C₆H₄—OCH₃ (p) | melting point: 114–115° C. | Boc-L-Valine |
| 24 | (CH₃)₃C— | H | H | —CH(CH₃)₂ | H | —CH₂—C₆H₃(Cl)₂ (2,5) | melting point: 121–122° C. | Boc-L-Valine |
| 25 | (CH₃)₃C— | H | H | —CH(CH₃)₂ | H | —CH₂—C₆H₄—CF₃ (p) | melting point: 120–121° C. | Boc-L-Valine |
| 26 | (CH₃)₃C— | H | H | —CH(CH₃)₂ | H | —C₆H₅ | melting point: 160–161° C. | Boc-L-Valine |
| 27 | (CH₃)₃C— | H | H | —CH(CH₃)₂ | H | —C₆H₄—CH₃ (p) | melting point: 133–134° C. | Boc-L-Valine |

TABLE 1-continued

| No. | R¹ | R² | R³ | R⁴ | R⁵ (N) R⁶ | physical constants | amino acid employed |
|---|---|---|---|---|---|---|---|
| 28 | (CH₃)₃C— | H | H | —CH(CH₃)₂ | H, 4-Cl-phenyl | melting point: 142–144° C. | Boc-L-Valine |
| 29 | (CH₃)₃C— | H | H | —CH(CH₃)₂ | H, 3,4-dichlorophenyl | melting point: 143–144° C. | Boc-L-Valine |
| 30 | (CH₃)₃C— | H | H | —CH(CH₃)₂ | H, 3,5-dichlorophenyl | melting point: 133–135° C. | Boc-L-Valine |
| 31 | (CH₃)₃C— | H | H | —CH(CH₃)₂ | H, —CH₂-(4-pyridyl) | melting point: 120–122° C. | Boc-L-Valine |
| 32 | (CH₃)₃C— | H | H | —CH(CH₃)₂ | H, —CH₂-(3-pyridyl) | melting point: 85–87° C. | Boc-L-Valine |
| 33 | (CH₃)₃C— | H | H | —CH(CH₃)₂ | H, —CH₂-(2-pyridyl) | melting point: 102–104° C. | Boc-L-Valine |
| 34 | (CH₃)₃C— | H | H | —CH(CH₃)₂ | H, 4-SCF₃-phenyl | melting point: 79–81° C. | Boc-L-Valine |

TABLE 1-continued

| No. | R¹ | R² | R³ | R⁴ | R⁵ ⟩N−R⁶ | physical constants | amino acid employed |
|---|---|---|---|---|---|---|---|
| 35 | (CH₃)₃C— | H | H | —CH(CH₃)₂ | H, 4-OCF₃-C₆H₄ | NMR: δ 0.9–1.0/ 1.4/ 7.0–7.1/ 7.4–7.5 | Boc-L-Valine |
| 36 | (CH₃)₃C— | H | H | —CH(CH₃)₂ | H, 4-CH₃-C₆H₄ | melting point: 127–129° C. | Boc-L-Valine |
| 37 | (CH₃)₃C— | H | H | —CH₂—CH(CH₃)₂ | H, —CH(CH₃)*-4-Cl-C₆H₄ | melting point: 141–143° C. *: R−(+)− | Boc-L-Leucine |
| 38 | (CH₃)₃C— | H | H | —CH₂—CH(CH₃)₂ | H, —CH(CH₃)-4-Cl-C₆H₄ | melting point: 119–121° C. | Boc-L-Leucine |
| 39 | (CH₃)₃C— | H | H | —CH(CH₃)—CH₂—CH₃ | H, —CH(CH₃)*-4-Cl-C₆H₄ | melting point: 178–180° C. *: R−(+)− | Boc-L-Isoleucine |
| 40 | (CH₃)₃C— | H | H | —CH(CH₃)—CH₂—CH₃ | H, —CH(CH₃)-4-Cl-C₆H₄ | melting point: 112–114° C. | Boc-L-Isoleucine |
| 41 | (CH₃)₃C— | H | H | —CH(CH₃)₂ | H, —CH(CH₃)*-4-Cl-C₆H₄ | melting point: 161–163° C. *: R−(+)− | Boc-D/L-Valine |
| 42 | (CH₃)₃C— | H | H | —CH(CH₃)₂ | H, —CH(CH₃)-4-Cl-C₆H₄ | melting point: 159–161° C. | Boc-D/L-Valine |

TABLE 1-continued

| No. | R¹' | R² | R³ | R⁴ | R⁵—N—R⁶ (R⁵) | (R⁶) | physical constants | amino acid employed |
|---|---|---|---|---|---|---|---|---|
| 43 | (CH₃)₃C— | H | H | —CH(CH₃)₂ | H | 4-OCH₃-phenyl | melting point: 173–175° C. | Boc-D/L-Valine |
| 44 | (CH₃)₃C— | H | H | —CH(CH₃)₂ | H | —CH₂—CN | melting point: 161–163° C. | Boc-D/L-Valine |
| 45 | CH₃—C(CH₃)(CCl₃)— | H | H | —CH(CH₃)₂ | H | —CH(CH₃)(4-Cl-phenyl) | melting point: 168–169° C. | Trichlorbutoxycarbonyl-L-Valine |
| 46 | CH₃—C(CH₃)(CCl₃)— | H | H | —CH(CH₃)₂ | H | —CH(CH₃)(4-Cl-phenyl) | melting point: 154–155° C. | Trichlorbutoxycarbonyl-D/L-Valine |
| 47 | CH₃—C(CCl₃)(CH₃)— | H | H | —CH(CH₃)₂ | H | 2-Cl-phenyl (with 4-Cl-phenyl-CH₂—) | melting point: 181–182° C. | Trichlorbutoxycarbonyl-L-Valine |
| 48 | (CH₃)₂C(CCl₃)— (with CH₃) | H | H | —CH(CH₃)₂ | H | —CH₂-(4-Cl-phenyl) | melting point: 150–151° C. | Trichlorbutoxycarbonyl-L-Valine |
| 49 | CH₃— | H | H | —CH(CH₃)₂ | H | —CH(CH₃)(4-Cl-phenyl) | melting point: 160–161° C. | Methoxycarbonyl-L-Valine |
| 50 | CH₃CH₂— | H | H | —CH(CH₃)₂ | H | —CH(CH₃)(4-Cl-phenyl) | melting point: 164–165° C. | Ethoxycarbonyl-L-Valine |
| 51 | CH₃—CH₂— | H | H | —CH(CH₃)₂ | H | —CH(CH₃)(4-Cl-phenyl) | melting point: 136–137° C. | Ethoxycarbonyl-D/L-Valine |

TABLE 1-continued

| No. | R¹' | R²' | R³' | R⁴' | R⁵' | R⁶' | physical constants | amino acid employed |
|---|---|---|---|---|---|---|---|---|
| 52 | CH₂=CHCH₂— | H | H | —CH(CH₃)₂ | H | —CH(CH₃)-C₆H₄-Cl (p) | melting point: 146–147° C. | Allyloxy-carbonyl-L-Valine |
| 53 | CH₂=CHCH₂— | H | H | —CH(CH₃)₂ | H | —C₆H₄-Cl (p) | melting point: 167–168° C. | Allyloxy-carbonyl-L-Valine |
| 54 | CH₂=CHCH₂— | H | H | —CH(CH₃)₂ | H | —CH₂-C₆H₄-Cl (p) | melting point: 170–171° C. | Allyloxy-carbonyl-L-Valine |
| 55 | CH₃CH₂CH₂CH₂— | H | H | —CH(CH₃)₂ | H | —CH(CH₃)-C₆H₄-Cl (p) | melting point: 172–173° C. | n-Butyloxy-carbonyl-L-Valine |
| 56 | CH₃CH₂CH₂CH₂— | H | H | —CH(CH₃)₂ | H | —C₆H₄-Cl (p) | melting point: 146–147° C. | n-Butyloxy-carbonyl-L-Valine |
| 57 | CH₃CH₂CH₂CH₂— | H | H | —CH(CH₃)₂ | H | —CH₂-C₆H₄-Cl (p) | melting point: 148–149° C. | n-Butyloxy-carbonyl-L-Valine |
| 58 | (CH₃)₂CHCH₂— | H | H | —CH(CH₃)₂ | H | —CH(CH₃)-C₆H₄-Cl (p) | melting point: 161–162° C. | i-Butyloxy-carbonyl-L-Valine |
| 59 | (CH₃)₂CHCH₂— | H | H | —CH(CH₃)₂ | H | —C₆H₄-Cl (p) | melting point: 160–162° C. | i-Butyloxy-carbonyl-L-Valine |

TABLE 1-continued

| No. | $R^{1'}$ | $R^{2'}$ | $R^{3'}$ | $R^{4'}$ | $R^{5'}$ $\diagdown$ N $\diagup$ $R^{6'}$ | | physical constants | amino acid employed |
|---|---|---|---|---|---|---|---|---|
| 60 | $(CH_3)_2CHCH_2-$ | H | H | $-CH(CH_3)_2$ | H | 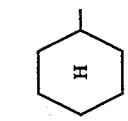 | melting point: 157–158° C. | i-Butyloxy-carbonyl-L-Valine |
| 61 | 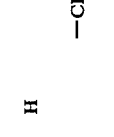 | H | H | $-CH(CH_3)_2$ | H | 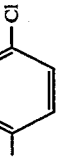 | melting point: 160–161° C. | Cyclohexyl-oxycarbonyl-L-Valine |
| 62 | 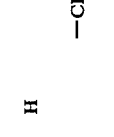 | H | H | $-CH(CH_3)_2$ | H |  | melting point: 195–197° C. | Cyclohexyl-oxycarbonyl-L-Valine |
| 63 | 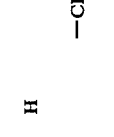 | H | H | $-CH(CH_3)_2$ | H |  | melting point: 180–181° C. | Cyclohexyl-oxycarbonyl-L-Valine |
| 64 | $CH_2=CH-CH_2-$ | H | H | $-CH(CH_3)_2$ | H |  | mp: 147–152° C. | Alkoxycar-bonyl-L-Valine |
| 65 | $CH_2=CH-CH_2-$ | H | H | $-CH_2-CH(CH_3)_2$ | H | 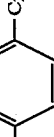 | mp: 163–167° C. | Alkoxycar-bonyl-L-Valine |
| 66 | $(CH_3)_3C$ | H | H | $-CH(CH_3)_2$ | H | 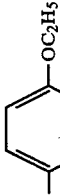 | | BOC-L-Leucine |
| 67 | 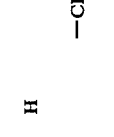 | H | H | $-CH(CH_3)_2$ | H |  | mp: 178–183° C. | Cyclohexyl-oxycarbonyl-L-Valine |

TABLE 1-continued

| No. | R$^1$ | R$^2$ | R$^3$ | R$^4$ | $R^5\diagdown N \diagup R^6$ | | physical constants | amino acid employed |
|---|---|---|---|---|---|---|---|---|
| 68 | cyclohexyl (H) | H | H | —CH(CH$_3$)$_2$ | —CH(CH$_3$)— | ⟨phenyl⟩—OC$_2$H$_5$, H | | mp: 177–183° C. | Cyclohexyl-carbonyl-L-Valine |
| 69 | cyclohexyl (H) | H | H | —CH(CH$_3$)$_2$ | —CH(CH$_3$)— | ⟨phenyl⟩—N(CH$_3$)$_2$, H | | mp: 124–128° C. | Cyclohexyl-oxycarbonyl-L-Valine |
| 70 | CH$_2$=CH—CH$_2$— | H | H | —CH(CH$_3$)$_2$ | —CH(CH$_3$)—CH$_2$— | ⟨phenyl⟩—OCH$_3$, H | | mp: 159–160° C. | Allyloxy-carbonyl-L-Valine |
| 71 | CH$_2$=CH—CH$_2$— | H | H | —CH(CH$_3$)$_2$ | —CH(C$_2$H$_5$)— | ⟨phenyl⟩—OCH$_3$, H | | mp: 168–170° C. | Allyloxy-carbonyl-L-Valine |
| 72 | CH$_2$=CH—CH$_2$— | H | H | —CH(CH$_3$)$_2$ | —CH(C$_2$H$_5$)— | ⟨phenyl⟩—CH$_3$, H | | mp: 170–171° C. | Allyloxy-carbonyl-L-Valine |
| 73 | cyclohexyl (H) | H | H | —CH(CH$_3$)$_2$ | —CH(CH$_3$)—CH$_2$— | ⟨phenyl⟩—OCH$_3$, H | | mp: 153–154° C. | Cyclohexyl-oxycarbonyl-L-Valine |
| 74 | cyclohexyl (H) | H | H | —CH(CH$_3$)$_2$ | —CH(C$_2$H$_5$)— | ⟨phenyl⟩—OCH$_3$, H | | mp: 164–168° C. | Cyclohexyl-oxycarbonyl-L-Valine |
| 75 | cyclohexyl (H) | H | H | —CH(CH$_3$)$_2$ | —CH(C$_2$H$_5$)— | ⟨phenyl⟩—CH$_3$, H | | mp: 151–152° C. | Cyclohexyl-oxycarbonyl-L-Valine |

TABLE 1-continued

| No. | R¹' | R²' | R³' | R⁴' | N-R⁵'/R⁶' | physical constants | amino acid employed |
|---|---|---|---|---|---|---|---|
| 76 | CH₂=CH—CH₂— | H | H | —CH(CH₃)₂ | H, —CH(CH₃)—CH₂—CH₂-(4-OCH₃-phenyl) | mp: 164–168° C. | Allyloxy-carbonyl-L-Valine |
| 77 | CH₂=CH—CH₂— | H | H | —CH(CH₃)₂ | H, —CH(CH₃)-(2-OCH₃-phenyl) | mp: 152–153° C. | Allyloxy-carbonyl-L-Valine |
| 78 | CH₂=CH—CH₂— | H | H | —CH(CH₃)₂ | H, —CH(CH₃)-(3-OCH₃-phenyl) | mp: 77–78° C. | Allyloxy-carbonyl-L-Valine |
| 79 | cyclohexyl (H) | H | H | —CH(CH₃)₂ | H, —CH(CH₃)—CH₂—CH₂-(4-OCH₃-phenyl) | mp: 167–171° C. | Cyclohexyl-oxycarbonyl-L-Valine |
| 80 | cyclohexyl (H) | H | H | —CH(CH₃)₂ | H, —CH(CH₃)-(2-OCH₃-phenyl) | mp: 169–172° C. | Cyclohexyl-oxycarbonyl-L-Valine |
| 81 | cyclohexyl (H) | H | H | —CH(CH₃)₂ | H, —CH(CH₃)-(3-OCH₃-phenyl) | mp: 158–163° C. | Cyclohexyl-oxycarbonyl-L-Valine |
| 82 | CH₂=CH—CH₂— | H | H | —CH(CH₃)₂ | H, —CH(C₂H₅)-(4-Cl-phenyl) | mp: 153–157° C. | Allyloxy-carbonyl-L-Valine |

TABLE 1-continued

| No. | R¹ | R² | R³ | R⁴ | R⁵ (N) R⁶ | (aryl) | physical constants | amino acid employed |
|---|---|---|---|---|---|---|---|---|
| 83 | $CH_2=CH-CH_2-$ | H | H | $-CH(CH_3)_2$ | H | $-CH(CH_3)$–C₆H₄–OCH₃ (4-) | mp: 152–153° C. | Allyloxy-carbonyl-L-Valine |
| 84 | $CH_2=CH-CH_2-$ | H | H | $-CH(CH_3)_2$ | H | $-CH(CH_3)$–C₆H₄–CH₃ (4-) | mp: 139–145° C. | Allyloxy-carbonyl-L-Valine |
| 85 | cyclohexyl | H | H | $-CH(CH_3)_2$ | H | $-CH(C_2H_5)$–C₆H₄–Cl (4-) | mp: 172–173° C. | Cyclohexyl-oxycarbonyl-L-Valine |
| 86 | cyclohexyl | H | H | $-CH(CH_3)_2$ | H | $-CH(CH_3)$–C₆H₄–OCH₃ (4-) | mp: 166–167° C. | Cyclohexyl-oxycarbonyl-L-Valine |
| 87 | cyclohexyl | H | H | $-CH(CH_3)_2$ | H | $-CH(CH_3)$–C₆H₄–CH₃ (4-) | mp: 167–180° C. | Cyclohexyl-oxycarbonyl-L-Valine |
| 88 | cyclohexyl | H | H | $-CH(CH_3)_2$ | H | $-CH(CH_3)$–C₆H₄–Cl (4-) | mp: 169–172° C. | Cyclohexyl-oxycarbonyl-L-Valine |
| 89 | cyclohexyl | H | H | $-CH(CH_3)_2$ | H | $-CH(CH_3)$–C₆H₄–Cl (2-) | mp: 177–180° C. | Cyclohexyl-oxycarbonyl-L-Valine |
| 90 | cyclohexyl | H | H | $-CH(CH_3)_2$ | H | $-CH(CH_3)$–C₆H₄–Cl (3-) | mp: 167–170° C. | Cyclohexyl-oxycarbonyl-L-Valine |

TABLE 1-continued

| No. | R¹ | R² | R³ | R⁴ | R⁵ N—R⁶ | | physical constants | amino acid employed |
|---|---|---|---|---|---|---|---|---|
| 91 | cyclohexyl | H | H | —CH(CH₃)₂ | H | 4-OCF₃-C₆H₄—CH(CH₃)— | mp: 183–187° C. | Cyclohexyl-carbonyl-L-Valine |
| 92 | cyclohexyl | H | H | —CH(CH₃)₂ | H | 3,4-Cl₂-C₆H₃—CH(CH₃)— | mp: 176–180° C. | Cyclohexyl-carbonyl-L-Valine |
| 93 | (CH₃)₂CH—CH₂— | H | H | —CH(CH₃)₂ | H | 4-CH₃-C₆H₄—CH(CH₃)— | mp: 160–166° C. | i-Butyloxy-carbonyl-L-Valine |
| 94 | (CH₃)₂CH—CH₂— | H | H | —CH(CH₃)₂ | H | 4-OCH₃-C₆H₄—CH(CH₃)— | mp: 154–158° C. | i-Butyloxy-carbonyl-L-Valine |
| 95 | (CH₃)₂CH—CH₂— | H | H | —CH(CH₃)₂ | H | 4-Cl-C₆H₄—CH(C₂H₅)— | mp: 150–151° C. | i-Butyloxy-carbonyl-L-Valine |
| 96 | (CH₃)₂CH—CH₂— | H | H | —CH(CH₃)₂ | H | 3,4-Cl₂-C₆H₃—CH(CH₃)— | mp: 172–176° C. | i-Butyloxy-carbonyl-L-Valine |
| 97 | (CH₃)₂CH—CH₂— | H | H | —CH(CH₃)₂ | H | 4-CH₃-C₆H₄—CH(C₂H₅)— | mp: 154–159° C. | i-Butyloxy-carbonyl-L-Valine |

TABLE 1-continued

| No. | R¹ | R² | R³ | R⁴ | $\overset{R^{5'}}{\underset{R^{6'}}{N-}}$ | | physical constants | amino acid employed |
|---|---|---|---|---|---|---|---|---|
| 98 | (CH₃)₂CH—CH₂— | H | H | —CH(CH₃)₂ | H | —CH(C₂H₅)— C₆H₄—OCH₃ (p) | mp: 164–170° C. | i-Butyloxy-carbonyl-L-Valine |
| 99 | cyclohexyl (H) | H | H | —CH(CH₃)₂ | H | —CH(CH₃)— C₆H₄—Cl (p) | mp: | Cyclohexyl-oxycarbonyl-L-Valine |
| 100 | CH₂=CH—CH₂— | H | H | —CH(C₂H₅)—CH₃ | H | —CH(CH₃)— C₆H₄—Cl (p) | mp: 178–180° C. | Allyloxycar-bonyl-L-Iso-leucine |
| 101 | (CH₃)₂CH—CH₂— | H | H | —CH(C₂H₅)—CH₃ | H | —CH(CH₃)— C₆H₄—Cl (p) | mp: 142–144° C. | i-Butyloxy-carbonyl-L-Isoleucine |
| 102 | CH₃—(CH₂)₃— | H | H | —CH(C₂H₅)—CH₃ | H | —CH(CH₃)— C₆H₄—Cl (p) | mp: 158–161° C. | n-Butyloxy-carbonyl-L-Isoleucine |
| 103 | CH₃—(CH₂)₂— | H | H | —CH(C₂H₅)—CH₃ | H | —CH(CH₃)— C₆H₄—Cl (p) | mp: 167–171° C. | n-Propyloxy-carbonyl-L-Isoleucine |
| 104 | CH₃—(CH₂)₅— | H | H | —CH(C₂H₅)—CH₃ | H | —CH(CH₃)— C₆H₄—Cl (p) | mp: 152–154° C. | n-Hexyloxy-carbonyl-L-Isoleucine |
| 105 | (CH₃)₃C— | H | —CH₂—CH₂—CH₂—CH₂—CH₂— | | H | —CH(CH₃)— C₆H₄—Cl (p) | mp: 198–199° C. | BOC-(1-Amino-cyclohexane-carboxylic acid) |

TABLE 1-continued

| No. | R¹' | R²' | R³' | R⁴' | R⁵'—N—R⁶' | | physical constants | amino acid employed |
|---|---|---|---|---|---|---|---|---|
| 106 | $(CH_3)_3C-$ | H | | $-CH_2-CH_2-CH_2-CH_2-$ | H | $-CH(CH_3)$—C₆H₄—$CH_3$ (p) | mp: 185–186° C. | BOC-(1-Aminocyclohexanecarboxylic acid) |
| 107 | $(CH_3)_3C-$ | H | | $-CH_2-CH_2-CH_2-CH_2-$ | H | $-CH(CH_3)$—C₆H₄—$OCH_3$ (p) | mp: 176–177° C. | BOC-(1-Aminocyclohexanecarboxylic acid) |
| 108 | $(CH_3)_3C-$ | H | | $-CH_2-CH_2-CH_2-CH_2-$ | H | $-CH(CH_3)$—C₆H₄—Cl (p) | mp: 193–196° C. | BOC-(1-Aminocyclohexanecarboxylic acid) |
| 109 | $(CH_3)_3C-$ | H | | $-CH_2-CH_2-CH_2-CH_2-$ | H | $-CH(CH_3)$—C₆H₄—$CH_3$ (p) | mp: 172–175° C. | BOC-(1-Aminocyclopentanecarboxylic acid) |
| 110 | $(CH_3)_3C-$ | H | | $-CH_2-CH_2-CH_2-CH_2-$ | H | $-CH(CH_3)$—C₆H₄—$OCH_3$ (p) | mp: 180–182° C. | BOC-(1-Aminocyclopentanecarboxylic acid) |
| 111 | $(CH_3)_3C-$ | H | H | $-CH-C_2H_5$<br>$\quad\ \ CH_3$ | H | $-CH(CH_3)$—C₆H₄—Cl (p) | mp: 145–147° C. | BOC-D,L-Isoleucine |
| 112 | $(CH_3)_3C-$ | H | H | $-CH-C_2H_5$<br>$\quad\ \ CH_3$ | H | $-CH(CH_3)$—C₆H₄—$CH_3$ (p) | mp: 145–147° C. | BOC-D,L-Isoleucine |
| 113 | $(CH_3)_3C-$ | H | H | $-CH-C_2H_5$<br>$\quad\ \ CH_3$ | H | $-CH(CH_3)$—C₆H₄—$OCH_3$ (p) | mp: 140–142° C. | BOC-D,L-Isoleucine |

TABLE 1-continued

| No. | R$^1$ | R$^2$ | R$^3$ | R$^4$ | R$^5$ / N / R$^6$ | | physical constants | amino acid employed |
|---|---|---|---|---|---|---|---|---|
| | | | | | R$^5$ | R$^6$ | | |
| 114 | (CH$_3$)$_3$C— | H | H | cyclohexyl | H | —CH(CH$_3$)—C$_6$H$_4$—Cl | mp: >250° C. | BOC-(α, (L)-Amino-cyclohexane acetic acid) |
| 115 | (CH$_3$)$_3$C— | H | H | cyclohexyl | H | —CH(CH$_3$)—C$_6$H$_4$—CH$_3$ | mp: 135–138° C. | BOC-(α, (L)-Amino-cyclohexane acetic acid) |
| 116 | (CH$_3$)$_3$C— | H | H | cyclohexyl | H | —CH(CH$_3$)—C$_6$H$_4$—OCH$_3$ | mp: >250° C. | BOC-(α-(L)-Amino-cyclohexane acetic acid) |
| 117 | (CH$_3$)$_3$C— | H | H | cyclopentyl | H | —CH(CH$_3$)—C$_6$H$_4$—Cl | mp: 169–172° C. | BOC-(α-(L)-Amino-cyclopentane acetic acid) |
| 118 | (CH$_3$)$_3$C— | H | H | cyclopentyl | H | —CH(CH$_3$)—C$_6$H$_4$—CH$_3$ | mp: 162–169° C. | BOC-(α, (L)-Amino-cyclopentane acetic acid) |
| 119 | (CH$_3$)$_3$C— | H | H | cyclopentyl | H | —CH(CH$_3$)—C$_6$H$_4$—OCH$_3$ | mp: 150–160° C. | BOC-(α-(L)-Amino-cyclopentane acetic acid) |
| 120 | (CH$_3$)$_3$C— | H | H | —CH(C$_2$H$_5$)—CH$_3$ | H | —CH(CH$_3$)—C$_6$H$_4$—Cl | mp: 136–137° C. | BOC-L-Isoleucine |
| 121 | cyclohexyl | H | H | —CH(CH$_3$)$_2$ | H | —CH(CH$_3$)-(3-pyridyl) | mp: 108–111° C. | Cyclohexyl-oxycarbonyl-L-Valine |

TABLE 1-continued

| No. | R¹' | R²' | R³' | R⁴' | R⁵'—N—R⁶' | physical constants | amino acid employed |
|---|---|---|---|---|---|---|---|
| 122 | cyclohexyl | H | H | —CH(CH₃)₂ | H, 2,4-dimethylphenyl | mp: 168–174° C. | Cyclohexyl-oxycarbonyl-L-Valine |
| 123 | cyclohexyl | H | H | —CH(CH₃)₂ | H, pyridin-4-yl | mp: 124–129° C. | Cyclohexyl-oxycarbonyl-L-Valine |
| 124 | cyclohexyl | H | H | —CH(CH₃)₂ | H, 3-(trifluoromethyl)phenyl | mp: 120–128° C. | Cyclohexyl-oxycarbonyl-L-Valine |
| 125 | cyclohexyl | H | H | —CH(CH₃)₂ | H, 3,5-diisopropylphenyl | mp: 140–142° C. | Cyclohexyl-oxycarbonyl-L-Valine |
| 126 | (CH₃)₃C— | H | H | CH₂—CH(CH₃)₂ | H, 4-methylphenyl | mp: 110–111° C. | BOC-L-Leucine |
| 127 | (CH₃)₃C— | H | H | —CH(CH₃)₂ | H, 4-(trifluoromethoxy)phenyl | mp: 79° C. | BOC-L-Valine |
| 128 | (CH₃)₃C— | H | H | —CH(CH₃)₂ | H, 3-chlorophenyl | mp: 114° C. | BOC-L-Valine |

TABLE 1-continued

| No. | R¹ | R² | R³ | R⁴ | $\begin{array}{c}R^5\diagdown N\diagup R^6\end{array}$ | | physical constants | amino acid employed |
|---|---|---|---|---|---|---|---|---|
| 129 | (CH₃)₃C— | H | H | —CH(CH₃)₂ | H | —CH(CH₃)—(2-OCH₃-phenyl) | mp: 114° C. | BOC-L-Valine |
| 130 | (CH₃)₃C— | H | H | —CH(CH₃)₂ | H | —CH(CH₃)—(3-OCH₃-phenyl) | mp: 93° C. | BOC-L-Valine |
| 131 | (CH₃)₃C— | H | H | —CH(CH₃)₂ | H | —CH(CH₃)—(4-OC₂H₅-phenyl) | mp: 138° C. | BOC-L-Valine |
| 132 | (CH₃)₃C— | H | H | —CH(CH₃)₂ | H | —CH(CH₃)—(4-C₂H₅-phenyl) | mp: 112° C. | BOC-L-Valine |
| 133 | (CH₃)₃C— | H | H | —CH(CH₃)₂ | H | —CH(CH₃)—(4-NO₂-phenyl) | mp: 130° C. | BOC-L-Valine |
| 134 | (CH₃)₃C— | H | H | —CH(CH₃)₂ | H | —CH(CH₃)—(4-CH₃-phenyl) | mp: 124° C. | BOC-L-Valine |
| 135 | (CH₃)₃C— | H | H | —CH(CH₃)₂ | H | —CH(C₂H₅)—(4-OCH₃-phenyl) | mp: 138° C. | BOC-L-Valine |

TABLE 1-continued

| No. | R¹ | R² | R³ | R⁴ | R⁵ (N-R⁶) | R⁶ | physical constants | amino acid employed |
|---|---|---|---|---|---|---|---|---|
| 136 | (CH₃)₃C— | H | H | —CH(CH₃)₂ | H | —CH(CH₃)—CH₂—C₆H₄—OCH₃ (4-) | mp: 63° C. | BOC-L-Valine |
| 137 | (CH₃)₃C— | H | H | —CH(CH₃)₂ | H | —C(CH₃)(CH₃)—C₆H₄—OCH₃ (4-) | mp: 94° C. | BOC-L-Valine |
| 138 | (CH₃)₃C— | H | H | —CH(CH₃)—C₂H₅ | H | —CH(CH₃)—C₆H₄—OCF₃ (4-) | mp: 96° C. | BOC-L-Isoleucine |
| 139 | (CH₃)₃C— | H | H | —CH(CH₃)—C₂H₅ | H | —CH(CH₃)—C₆H₄—Cl (3-) | mp: 123° C. | BOC-L-Isoleucine |
| 140 | (CH₃)₃C— | H | H | —CH(CH₃)—C₂H₅ | H | —CH(CH₃)—C₆H₄—OCH₃ (2-) | mp: 105° C. | BOC-L-Isoleucine |
| 141 | (CH₃)₃C— | H | H | —CH(CH₃)—C₂H₅ | H | —CH(CH₃)—C₆H₄—OCH₃ (3-) | mp: 130° C. | BOC-L-Isoleucine |
| 142 | (CH₃)₃C— | H | H | —CH(CH₃)—C₂H₅ | H | —CH(CH₃)—C₆H₄—OC₂H₅ (4-) | | BOC-L-Isoleucine |

TABLE 1-continued

| No. | R1' | R2' | R3' | R4' | R5'⟍N⟋R6' | | physical constants | amino acid employed |
|---|---|---|---|---|---|---|---|---|
| 143 | (CH₃)₃C— | H | H | —CH—C₂H₅<br>　│<br>　CH₃ | H | —CH(CH₃)—C₆H₄—C₂H₅ (p) | mp: 82° C. | BOC-L-Isoleucine |
| 144 | (CH₃)₃C— | H | H | —CH—C₂H₅<br>　│<br>　CH₃ | H | —CH(C₂H₅)—C₆H₄—Cl (p) | mp: 134° C. | BOC-L-Isoleucine |
| 145 | (CH₃)₃C— | H | H | —CH—C₂H₅<br>　│<br>　CH₃ | H | —CH(C₂H₅)—C₆H₄—CH₃ (p) | mp: 121° C. | BOC-L-Isoleucine |
| 146 | (CH₃)₃C— | H | H | —CH—C₂H₅<br>　│<br>　CH₃ | H | —CH(C₂H₂)—C₆H₄—OCH₃ (p) | mp: 135° C. | BOC-L-Isoleucine |
| 147 | (CH₃)₃C— | H | H | —CH—C₂H₅<br>　│<br>　CH₃ | H | —CH(CH₃)—CH₂—C₆H₄—OCH₃ (m) | mp: 116° C. | BOC-L-Isoleucine |
| 148 | (CH₃)₃C— | H | H | —CH—C₂H₅<br>　│<br>　CH₃ | H | —CH(CH₃)—(CH₂)₂—C₆H₄—OCH₃ (p) | mp: 111° C. | BOC-L-Isoleucine |

Example A

Plasmopara test (vines)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and then kept in a humidity chamber at 20° to 22° C. and 100% relative atmospheric humidity for 1 day. The plants are then placed in a greenhouse at 22° C. and about 80% atmospheric humidity for 5 days. The plants are then moisened and placed in a humidity chamber for 1 day.

Evaluation is carried out 7 days after the inoculation.

In this test, for example, the compounds according to the following Preparation Examples exhibit activity:

TABLE A

Plasmopara test (vines) / protective

| Active compound | Degree of action in % of the untreated control at an active compound concentration of 5 ppm |
|---|---|
| (19) (known) $(CH_3)_3C-O-CO-NH-CH(CH(CH_3)_2)-CO-NH-CH_2-C_6H_5$ | 29 |
| (8) $(CH_3)_3C-O-CO-NH-CH(CH(CH_3)_2)-CO-NH-CH(CH_3)-C_6H_4-Cl$ | 100 |
| (61) $C_6H_{11}-O-CO-NH-CH(CH(CH_3)_2)-CO-NH-CH(CH_3)-C_6H_4-Cl$ | 94 |
| (52) $CH_2=CH-CH_2-O-CO-NH-CH(CH(CH_3)_2)-CO-NH-CH(CH_3)-C_6H_4-Cl$ | 94 |
| (51) $CH_3-CH_2-O-CO-NH-CH(CH(CH_3)_2)-CO-NH-CH(CH_3)-C_6H_4-Cl$ | 94 |
| (4) $(CH_3)_3C-O-CO-NH-CH(CH(CH_3)_2)-CO-NH-CH(CH_3)-C_6H_4-CH_3$ | 100 |

TABLE A-continued

Plasmopara test (vines) / protective

| Active compound | Degree of action in % of the untreated control at an active compound concentration of 5 ppm |
|---|---|
| 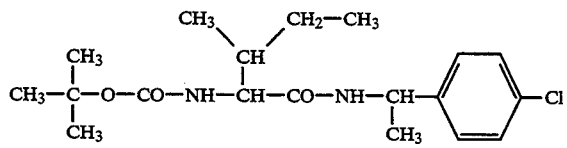<br>(39) | 91 |

Example B

Phytophthora test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabin at 100% relative atmospheric humidity and about 20° C.

Evaluation is carried out 3 days after the inoculation.

The compounds according to Preparation Examples (7), (40) and (41), for example, exhibit an excellent degree of action at an active compound concentration of, for example, 5 ppm.

TABLE B

Phytophthora test (tomato) / protective

| Active compound | Degree of action in % of the untreated control at an active compound concentration of 5 ppm |
|---|---|
| Known:<br>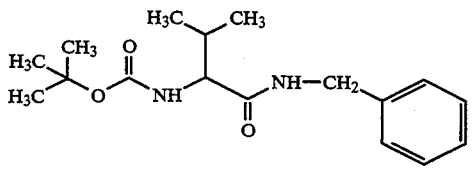 | 0 |
| According to the invention:<br>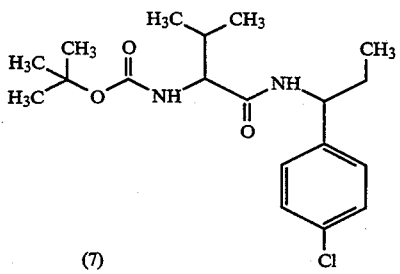<br>(7) | 85 |
| 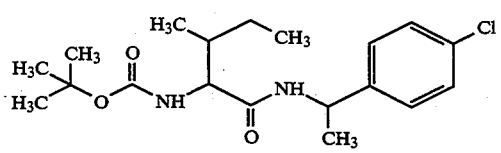<br>(40) | 80 |

TABLE B-continued

Phytophthora test (tomato) / protective

| Active compound | Degree of action in % of the untreated control at an active compound concentration of 5 ppm |
|---|---|
| <br>(41) | 80 |

It will be appreciated that the instant specification and claims are set forth by way of illustration and not limitation, and that various modifications and changes may be made without departing from the spirit and scope of the present invention.

What is claimed is:

1. A substituted amino amide derivative of the formula

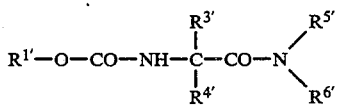

in which $R^{1'}$ represents straight-chain or branched alkyl having 1 to 6 carbon atoms, straight-chain or branched alkenyl or alkinyl having 2 to 6 carbon atoms, straight-chain or branched halogenoalkyl having 1 to 6 carbon atoms and 1 to 9 identical or different halogen atoms, straight-chain or branched halogenoalkenyl or halogenoalkinyl having 2 to 6 carbon atoms and 1 to 9 identical or different halogen atoms or unsubstituted or substituted cycloalkyl or cycloalkenyl having 3 to 7 carbon atoms, $R^{3'}$ represents hydrogen, and $R^{4'}$ represents i-propyl, i-butyl, s-butyl or 3-pentyl, or $R^{3'}$ and $R^{4'}$, together with the carbon atom to which they are bonded, form a cycloalkyl ring having 3 to 7 carbon atoms, $R^{5'}$ represents hydrogen or alkyl having 1 to 6 carbon atoms, and $R^{6'}$ represents alkenyl or alkinyl having in each case 2 to 6 carbon atoms, or represents cyanoalkyl having 1 to 4 carbon atoms in the alkyl part, phenylalkyl having 1 to 4 carbon atoms in the alkyl part, which is substituted in the phenyl part by one to three identical or different substitutents, or phenyl which is substituted by one to three identical or different substituents, the substituents in each case being selected from the group consisting of halogen; alkyl, alkoxy and alkylthio having in each case 1 to 4 carbon atoms; halogenoalkyl, halogenoalkoxy and halogenoalkylthio having in each case 1 to 4 carbon atoms and 1 to 9 identical or different halogen atoms; hydroxyl; cyano; nitro; amino; alkylamino and dialkylamino having in each case 1 to 4 carbon atoms and carboxyl; or represents cycloalkyl having 3 to 7 carbon atoms which is unsubstituted or substituted by identical or different substitutents, the substituents being alkyl and alkoxy and having in each case 1 to 4 carbon atoms.

2. A fungicidal composition comprising a fungicidally effective amount of a compound according to claim 1, and a diluent.

3. A substituted amino acid amide derivative of the formula:

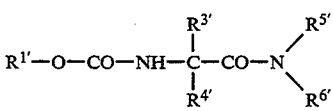

in which $R^{1'}$ represents straight-chain or branched alkyl having 1 to 6 carbon atoms, straight-chain or branched alkenyl or alkynyl having 2 to 6 carbon atoms, straight-chain or branched halogenoalkyl having 1 to 6 carbon atoms and 1 to 9 identical or different halogen atoms, straight-chain or branched halogenoalkenyl or halogenoalkynyl having 2 to 6 carbon atoms and 1 to 9 identical or different halogen atoms or unsubstituted or substituted cycloalkyl or cycloalkenyl having 3 to 7 carbon atoms;

$R^{3'}$ represents hydrogen; and $R^{4'}$ represents i-propyl, i-butyl, s-butyl or 3-pentyl; or $R^{3'}$ and $R^{4'}$ together with the carbon atom to which they are bonded form a cycloalkyl ring having 3 to 7 carbon atoms;

$R^{5'}$ represents hydrogen or alkyl having 1 to 6 carbon atoms; and $R^{6'}$ represents alkenyl or alkynyl having in each case 2 to 6 carbon atoms, or represents cyanoalkyl having 1 to 4 carbon atoms in the alkyl part, phenylalkyl having 1 to 4 carbon atoms in the alkyl part, which is substituted in the phenyl part by one to three identical or different substituents, the substituents in each case being selected from the group consisting of halogen, alkyl, alkoxy and alkylthio, each of which has 1 to 4 carbon atoms, halogenoalkyl, halogenoalkoxy and halogenoalkylthio, each of which has 1 to 4 carbon atoms and 1 to 9 identical or different halogen atoms, hydroxyl, cyano, nitro, amino, alkylamino and dialkylamino, each of which has 1 to 4 carbon atoms, and carboxyl, or $R^{6'}$ represents cycloalkyl having 3 to 7 carbon atoms and which is unsubstituted or substituted by identical or different substituents, the substituents being alkyl and alkoxy, each of which has 1 to 4 carbon atoms.

4. A fungicidal composition comprising a fungicidally effective amount of a compound according to claim 3, and a diluent.

* * * * *

UNITED STATES PATENT AND TRADEMARK OFFICE
CERTIFICATE OF CORRECTION

PATENT NO. : 5,411,987
DATED : May 2, 1995
INVENTOR(S) : Wollweber, et al.

It is certified that error appears in the above-indentified patent and that said Letters Patent is hereby corrected as shown below:

Column 59, line 22 after "amino" insert --acid--.

Signed and Sealed this

Tenth Day of October, 1995

BRUCE LEHMAN

Attest:

Attesting Officer

Commissioner of Patents and Trademarks